United States Patent
Tien et al.

(10) Patent No.: US 10,144,692 B2
(45) Date of Patent: Dec. 4, 2018

(54) METHOD OF MAKING VITAMIN K1

(71) Applicant: Sunny Pharmtech Inc., New Taipei (TW)

(72) Inventors: Jien-Heh Tien, Hayward, CA (US); Chu-Yi Pang, Taipei (TW); Nai-Hsuan Hsu, Taipei (TW)

(73) Assignee: SUNNY PHARMTECH INC., New Taipei (TW)

( * ) Notice: Subject to any disclaimer, the term of this patent is extended or adjusted under 35 U.S.C. 154(b) by 0 days.

(21) Appl. No.: 15/312,328

(22) PCT Filed: Oct. 16, 2014

(86) PCT No.: PCT/US2014/060925
§ 371 (c)(1),
(2) Date: Nov. 18, 2016

(87) PCT Pub. No.: WO2016/060670
PCT Pub. Date: Apr. 21, 2016

(65) Prior Publication Data
US 2017/0260117 A1    Sep. 14, 2017

(51) Int. Cl.
*C07C 46/06* (2006.01)
*C07C 46/00* (2006.01)

(52) U.S. Cl.
CPC .............. *C07C 46/06* (2013.01); *C07C 46/00* (2013.01)

(58) Field of Classification Search
None
See application file for complete search history.

(56) References Cited

U.S. PATENT DOCUMENTS

| | | | | |
|---|---|---|---|---|
| 2,334,669 A | * | 11/1943 | Baker | C07C 43/23 552/299 |
| 2,839,570 A | | 6/1958 | Lindlar | |
| 2,906,780 A | * | 9/1959 | Hirschmann | C07C 46/06 552/299 |
| 5,523,396 A | * | 6/1996 | Sato | C07C 303/28 430/190 |

FOREIGN PATENT DOCUMENTS

| WO | WO 96/28413 | * | 9/1996 |
|---|---|---|---|
| WO | WO9628413 A1 | | 9/1996 |

OTHER PUBLICATIONS

Huang, Synthetic Communication, 2006, 2667-2684.*

* cited by examiner

*Primary Examiner* — Ana Z Muresan
(74) *Attorney, Agent, or Firm* — WPAT, PC

(57) ABSTRACT

This invention discloses a method of making vitamin K1. The mentioned method of making vitamin K1 comprises performing a first one-pot synthesis with base catalyst, performing a first hydrolysis, performing a substitution, and performing a second one-pot synthesis without metal oxidant. The starting material of this invention is stable 2-methyl-1,4-naphthoquinone. Preferably, this invention provides a method of making vitamin K1 efficiently on simplifying the operation and decreasing the side-product. More preferably, without metal residue, the vitamin K1 of this invention is without metal residue and more safety for clinical application.

9 Claims, No Drawings

METHOD OF MAKING VITAMIN K1

BACKGROUND OF THE INVENTION

1. Field of the Invention

The present invention is generally related to a method of making vitamin K1, and more particularly to a method of making vitamin K1 without metal oxidant.

2. Description of the Prior Art

Vitamin K is also called as antihemorrhagic vitamin. In 1929, it is found that there are two forms, K1 and K2, of vitamin K in the natural.

There are many researches of making vitamin K1 in the prior art. For example, in U.S. Pat. Nos. 2,683,176 and 2,325,681, the vitamin K1 is obtained from 2-methyl-1,4-naphthohydroquinone as the starting material. 2-methyl-1,4-naphthohydroquinone is also used as the starting material in many literatures, such as *J. Am. Chem. Soc.,* 1940, 62 (10), pp 2861-2866, *J. Am. Chem. Soc.,* 1939,61, 3467-3475, *Agr. Biol. Chem.,* 1965, 29, 978-983, and *J. Am. Chem. Soc.,* 1937, 59(2), 392. However, it is known that 2-methyl-1,4-naphthohydroquinone is easily to be oxidized and very unstable. Therefore, there will be by-products formed during the manufacturing and the yield of the manufacturing will be decreased.

Moreover, in many literatures, metal oxidant is usually used in the manufacturing of vitamin K1, such as *J. Am. Chem. Soc.,* 1940, 62 (10), pp 2861-2866, and *Agr. Biol. Chem.,* 1965, 29, 978-983. It should be noticed that antihemorrhagic vitamin is possible be used on an emergently clinical patient, and the metal residue in the antihemorrhagic vitamin could be toxic and fatal to the emergently clinical patient.

In view of the above matters, developing a novel method of making vitamin K1 having the advantage of efficiently decreasing by-product formed during the manufacturing and no metal oxidant used in the manufacturing is still an important task for the industry.

SUMMARY OF THE INVENTION

In light of the above background, in order to fulfill the requirements of the industry, the present invention provides a novel method of making vitamin K1 having the advantage of efficiently decreasing by-product formed during the manufacturing and no metal oxidant used in the manufacturing, so that the mentioned method can be employed for making vitamin K1 more safety and efficiently.

One objective of the present invention is to provide a method of making vitamin K1 to increase the efficiency of the manufacturing of vitamin K1 through using stable starting material to decrease by-product formed during the manufacturing.

Another objective of the present invention is to provide a method of making vitamin K1 to increase the efficiency of the manufacturing of vitamin K1 through using one-pot synthesis to simplify the manufacturing operation and decrease by-product formed during the manufacturing.

Still another objective of the present invention is to provide a method of making vitamin K1 to increase the product safety on clinical application though using no metal oxidant during the manufacturing.

Accordingly, the present invention discloses a method of making vitamin K1. The mentioned method of making vitamin K1 comprises performing hydrogenation in situ esterification through a first one-pot synthesis to produce 2-methyl-1,4-naphthohydroquinone di-alkyl ester from 2-methyl-1,4-naphthoquinone with a base catalyst, performing a first hydrolysis procedure to produce 2-methyl-1,4-naphthohydroquinone mono-alkyl ester from 2-methyl-1,4-naphthohydroquinone di-alkyl ester, performing a substitution procedure to have 2-methyl-1,4-naphthohydroquinone mono-alkyl ester react with phytol/phytol derivatives to generate 2-methyl-3-phytyl-1,4-naphthohydroquinone mono-alkyl ester, and performing a second one-pot synthesis to form vitamin K1 from 2-methyl-3-phytyl-1,4-naphthohydroquinone mono-alkyl ester.

In one preferred example of this invention, the first one-pot synthesis includes a hydrogenation procedure and an esterification procedure in situ. According to this invention, the first one-pot synthesis is driven with a base catalyst. In one preferred example of this invention, the base catalyst is amine. The mentioned base catalyst is selected from one of the group consisting of the following: 4-dimethylaminopyridine (DMAP), triethylamine (TEA), 4-methyl-morpholine, dimethylaniline, methyl nicotinate, imidazole, pyridine, methyl pyridine. Preferably, the first one-pot synthesis does begin with a more stable starting material (2-methyl-1,4-naphthoquinone), and the unstable product of the hydrogenation, 2-methyl-1,4-naphthohydroquinone, does not be isolated. Therefore, according to this invention, the mentioned first one-pot synthesis can efficiently decrease by-product during the manufacturing of vitamin K1 and simplify the operation.

In one preferred example of this invention, the mentioned first hydrolysis procedure is performed with an organic base. In one preferred example, the mentioned organic base is an amine with stereo effect. The organic base is helpful to process a homogeneous hydrolysis, and the residue organic base is easily removed after the reaction.

In one preferred example of this invention, the mentioned second one-pot synthesis includes a second hydrolysis in situ oxidation procedure. It should be noticed that there is no metal oxidant used in the second one-pot synthesis. Without using metal oxidant, it can be ensured that there is no metal residue in the produced vitamin K1, so that the product can be more safe than the vitamin K1 produced from the method with metal oxidant in the prior art on medical application.

DESCRIPTION OF THE PREFERRED EMBODIMENTS

What probed into the invention is a method of making vitamin K1. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One preferred embodiment according to this specification discloses a method of making vitamin K1. The mentioned method comprises performing hydrogenation in situ esterification through a first one-pot synthesis to produce 2-methyl-1,4-naphthohydroquinone di-alkyl ester from 2-methyl-1,4-naphthoquinone with a base catalyst, performing a first hydrolysis procedure with an organic base to produce 2-methyl-1,4-naphthohydroquinone mono-alkyl ester from the 2-methyl-1,4-naphthohydroquinone di-alkyl ester, performing a substitution procedure to have the 2-methyl-1,4-naphthohydroquinone mono-alkyl ester react with phytol/or phytol derivatives to generate 2-methyl-3-phytyl-1,4-naphthohydroquinone mono-alkyl ester, and performing a second one-pot synthesis to form vitamin K1 from the 2-methyl-3-phytyl-1,4-naphthohydroquinone mono-alkyl ester.

According to this embodiment, firstly, 2-methyl-1,4-naphthohydroquinone di-alkyl ester is obtained from 2-methyl-1,4-naphthoquinone through said first one-pot synthesis. There is a hydrogenation in situ esterification procedure accomplished in the first one-pot synthesis. The mentioned first one-pot synthesis is performed with a base catalyst. In one preferred example of this embodiment, the base catalyst is amine. In one preferred example, the mentioned base catalyst is selected from at least one of the group consisted of the following: 4-dimethylaminopyridine (DMAP), triethylamine (TEA), 4-methyl-morpholine, dimethylaniline, methyl nicotinate, imidazole, pyridine, methyl pyridine. The mentioned first one-pot synthesis can be shown as the following.

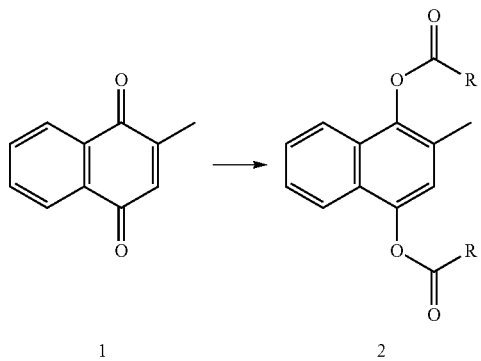

In the above-mentioned formula, R is C1-C20 alkyl group. Preferably, R is selected from one of the group consisted of the following: C1-C20 linear alkyl group, C3-C20 branch alkyl group, C3-C20 cyclic alkyl group.

Substantially, a first hydrolysis procedure is performed to obtain 2-methyl-1,4-naphthohydroquinone mono-alkyl ester. The mentioned organic base in the first hydrolysis procedure is an amine with stereo effect. Through stereo effect, the first hydrolysis can selectively hydrolyze one alkyl ester of 2-methyl-1,4-naphthohydroquinone di-alkyl ester. In one preferred example, the organic base in the first hydrolysis procedure is selected from at least one of the group consisted of the following: diisopropylamine, dicyclohexylamine. The mentioned first hydrolysis procedure can be shown as the following.

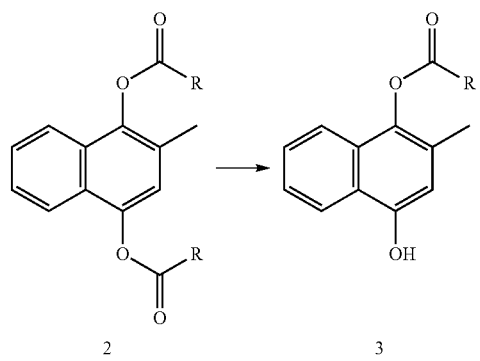

A substitution procedure is performed to have the 2-methyl-1,4-naphthohydroquinone mono-alkyl ester react with phytol/or phytol derivatives to generate 2-methyl-3-phytyl-1,4-naphthohydroquinone mono-alkyl ester. In one preferred example of this embodiment, the mentioned phytol derivatives can be selected from at least one of the group consisted of the following: phytol ester, phytol halide, isophytol. The mentioned substitution procedure can be shown as the following.

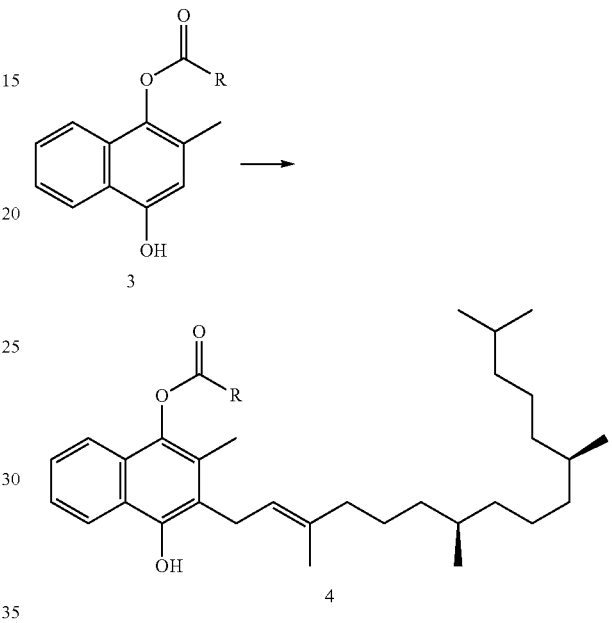

To produce vitamin K1, a second one-pot synthesis is performed to the 2-methyl-3-phytyl-1,4-naphthohydroquinone mono-alkyl ester. In one preferred example of this embodiment, a second hydrolysis in situ oxidation procedure is accomplished in the mentioned second one-pot synthesis. Preferably, according to this embodiment, it is not necessary to isolate the product of the second hydrolysis procedure, so that the operation of the manufacturing of vitamin K1 can be simplified. More preferably, there is no metal oxidant used in the mentioned oxidation procedure, and there is no metal residue formed with the produced vitamin K1. That is, the vitamin K1 of this embodiment can be more safe than the vitamin K1 produced from the method with metal oxidant in the prior art on medical application. The mentioned second one-pot synthesis can be shown as the following.

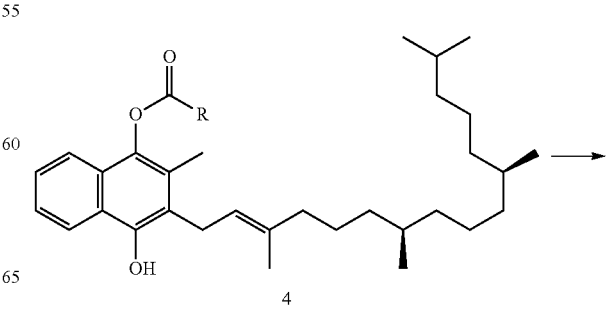

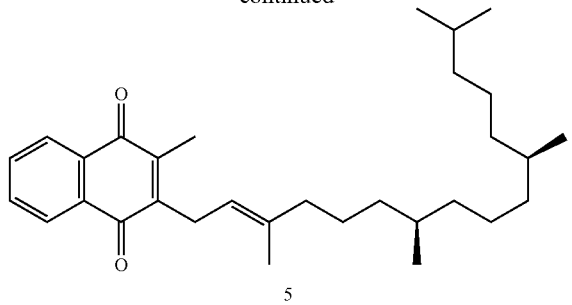

5

Another preferred embodiment according to this specification discloses a method of making vitamin K1. The mentioned method comprises reacting 2-methyl-1,4-naphthoquinone with carboxylic acid derivatives in the presence of a base catalyst under hydrogen to form 2-methyl-1,4-naphthohydroquinone di-alkyl ester, reacting the 2-methyl-1,4-naphthohydroquinone di-alkyl ester with an organic base to produce 2-methyl-1,4-naphthohydroquinone mono-alkyl ester, reacting the 2-methyl-1,4-naphthohydroquinone mono-alkyl ester with phytol/phytol derivatives to form 2-methyl-3-phytyl-1,4-naphthohydroquinone mono-alkyl ester, and performing a hydrolysis in situ oxidation procedure to the 2-methyl-3-phytyl-1,4-naphthohydroquinone mono-alkyl ester to form vitamin K1.

According to this embodiment, the carboxylic acid derivarives, reacting with 2-methyl-1,4-naphthoquinone, is selected from one of the group consisting of the following: acyl anhydride, acyl halide, active ester of HOSu (N-Hydroxysuccinimide), active ester of HOBt (1-Hydroxybenzotriazole). The base catalyst can be amine. In one preferred example of this embodiment, the base catalyst is selected from one of the group consisting of the following: 4-dimethylaminopyridine (DMAP), triethylamine (TEA), 4-methyl-morpholine, dimethylaniline, methyl nicotinate, imidazole, pyridine, methyl pyridine. In one preferred example of this embodiment, the reaction from 2-methyl-1,4-naphthoquinone to 2-methyl-1,4-naphthohydroquinone di-alkyl ester is an one-pot reaction. In one preferred example of this embodiment, the reaction from 2-methyl-1,4-naphthoquinone to 2-methyl-1,4-naphthohydroquinone di-alkyl ester is a hydrogenation in situ esterification procedure. The mentioned reaction from 2-methyl-1,4-naphthoquinone to 2-methyl-1,4-naphthohydroquinone di-alkyl ester can be presented as the following.

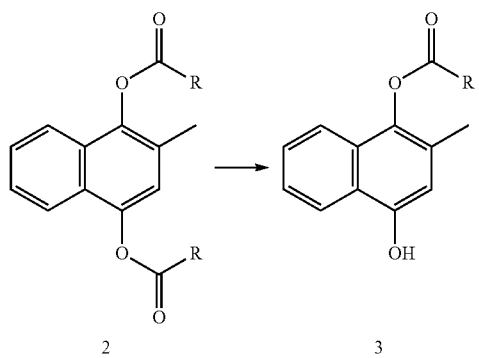

In the above-mentioned formula, R is C1-C20 alkyl group. Preferably, R is selected from one of the group consisted of the following: C1-C20 linear alkyl group, C3-C20 branch alkyl group, C3-C20 cyclic alkyl group.

According to this embodiment, the mentioned organic base, reacting with the 2-methyl-1,4-naphthohydroquinone di-alkyl ester, is an amine with stereo effect. In one preferred example, the mentioned organic base is selected from at least one of the group consisted of the following: diisopropylamine, dicyclohexylamine. The reaction from 2-methyl-1,4-naphthohydroquinone di-alkyl ester to 2-methyl-1,4-naphthohydroquinone mono-alkyl ester can be presented as the following.

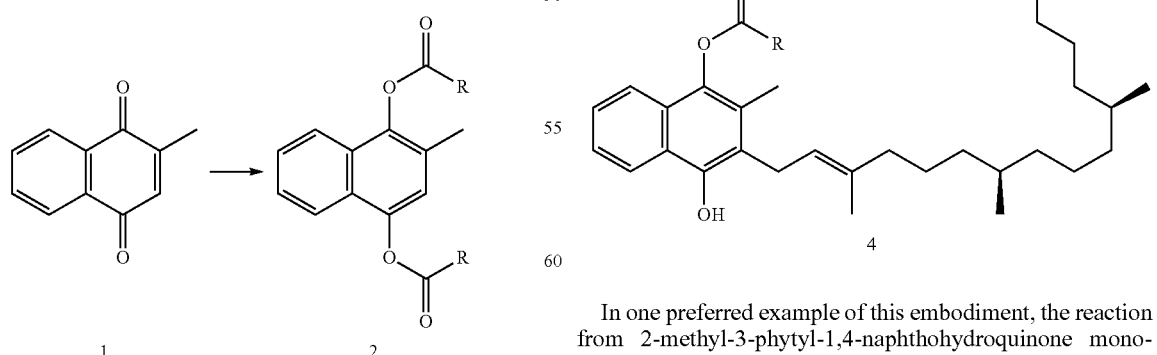

According to this embodiment, the phytol derivatives, reacting with the 2-methyl-1,4-naphthohydroquinone mono-alkyl ester, can be selected from one of the group consisted of the following: phytol, phytol ester, phytol halide, isophytol. The reaction from 2-methyl-1,4-naphthohydroquinone mono-alkyl ester to 2-methyl-3-phytyl-1,4-naphthohydroquinone mono-alkyl ester can be presented as the following.

In one preferred example of this embodiment, the reaction from 2-methyl-3-phytyl-1,4-naphthohydroquinone mono-alkyl ester to vitamin K1 is an one-pot reaction. In the above-mentioned reaction for forming vitamin K1 from 2-methyl-3-phytyl-1,4-naphthohydroquinone mono-alkyl ester, a hydrolysis in situ oxidation procedure is performed.

And, according to this embodiment, there is no metal oxidant used in the hydrolysis in situ oxidation procedure. Therefore, the vitamin K1 of this embodiment is more safety on medical application. The reaction from 2-methyl-3-phytyl-1,4-naphthohydroquinone mono-alkyl ester to vitamin K1 can be presented as the following.

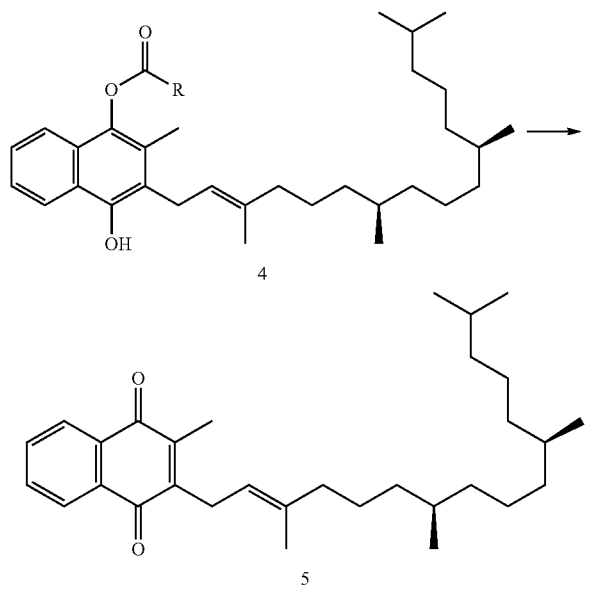

The preferred examples of the method of making vitamin K1 according to the invention are described in the following. However, the scope of the invention should be based on the claims, but is not restricted by the following examples.

EXAMPLE 1

Synthesis of 2-methyl-1,4-naphthohydroquinone di-acetate (3)

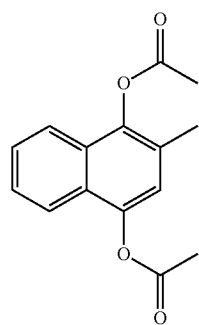

2-methyl-1,4-naphthoquinone (1) (20.0 g) was dissolved in ethyl acetate (200 g). Acetic anhydride (29.65 g), DMAP (1.42 g) and Pd/C (0.6 g) were added. The mixture was stirred at room temperature under hydrogen overnight. Pd/C was filtered out and the filtered liquor was washed with brine. The organic layer was concentrating and recrystallized in water (60 g) and IPA (80 g) solution, thereby obtaining 28.0 g of the title compound as white crystals (yield: 84.2%, HPLC purity: 99.8%). The compound was characterized by $^1$H-NMR: δ 2.27, s, 3H; 2.46, s, 3H; 2.50, s, 3H; 7.27, s, 1H; 7.55-7.62, m, 2H; 7.85-7.89, d, 2H.

The results of a study of the effect of different base catalyst are given in the following Table 1.

TABLE 1

Catalyst and conversion in diacetate in 2-methyl-1,4-naphthohydroquinone diacetate synthesis

| Expt | catalyst | Catalyst (%-mol) | Rxn time (hrs) | Conversion (%) |
|---|---|---|---|---|
| 1 | No catalyst | 10 | 6 | 0.77 |
| 2 | DMAP | 10 | 4 | 94.68 |
| 3 | triethylamine | 10 | 4 | 47.39 |
|   |   |   | 24 | 73.75 |
| 4 | 4-methylmorpholine | 10 | 4 | 31.46 |
|   |   |   | 24 | 71.14 |
| 5 | dimethylaniline | 10 | 4 | 6.25 |
| 6 | methyl nicotinate | 10 | 4 | 3.31 |
|   |   |   | 24 | 13.77 |
| 7 | imidazole | 10 | 4 | 11.85 |
|   |   |   | 24 | 46.88 |
| 8 | 2-hydroxypyridine | 10 | 4 | 0 |

EXAMPLE 2

Synthesis of 2-methyl-1,4-naphthohydroquinone dipropionate (3a)

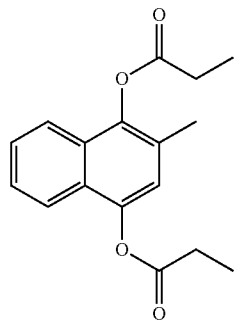

2-methyl-1,4-naphthoquinone (1) (10.0 g) was dissolved in ethyl acetate (100 g). Propionic anhydride (30.23 g), DMAP (0.71 g) and Pd/C (0.3 g) were added. The mixture was stirred at room temperature under hydrogen overnight. Pd/C was filtered out and the filtered liquor was washed with brine. The organic layer was concentrating and recrystallized in water (25 g) and 95% ethanol (21 g) solution, thereby obtaining 9.21 g of the title compound as white crystals (yield: 83.3%, HPLC purity: 99.4%). The compound was characterized by $^1$H-NMR: δ 1.21-1.26, m, 6H; 2.25, s, 3H; 2.80-2.88, m, 4H; 7.27, s, 1H; 7.55-7.62, m, 4H.

EXAMPLE 3

Synthesis of 2-methyl-1,4-naphthohydroquinone monoacetate (4)

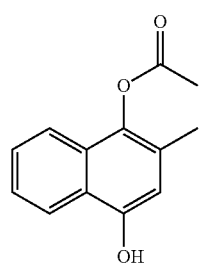

(4)

2-methyl-1,4-naphthohydroquinone diacetate (3) (23.3 g) were in methanol (116.5 g) and water (11.6 g). Di-isopropylamine (9.04 g) was added and stirred at 20-25° C. When the reaction was complete, the mixture was quenched with $HCl_{(aq)}$ and then extracted with ethyl acetate. The organic layer was washed with brine for twice. It was concentrated under reduce pressure and the crude was re-crystallized with ethyl acetate (35 g) and Heptane (116 g), thereby obtaining 13.53 g the title compound. (Yield: 69.3%, HPLC purity: 99.9%). The compound was characterized by $^1$H-NMR: δ 1.21, t, 3H; 2.17, s, 3H; 2.77-2.81, m, 2H; 6.74, s, 1H; 7.41-7.51, m, 2H; 7.67-7.68, d, 1H.; 8.10-8.12, d, 1H; 10.10, s, 1H.

TABLE 2

Amine and product purity in 2-Methyl-1,4-naphthohydroquinone Monoacetate synthesis

| Expt. | Amine | Molar ratio (3/amine) | Rxn time (hrs) | HPLC area % | | |
|---|---|---|---|---|---|---|
| | | | | (4) [a] | (1) [a] | (3) [a] |
| 1 | diisopropylamine | 1:1 | 3 | 96.55 | 0.25 | 0.59 |
| 2 | dicyclohexylamine | 1:1 | 3 | 96.04 | 0 | 1.8 |
| | | | 4 | 96.29 | 0 | 0.35 |

[a] (4): compound (4); (1): compound (1); (3): compound (3)

EXAMPLE 4

Synthesis of 2-Methyl-1,4-naphthohydroquinone Monopropionate (4a)

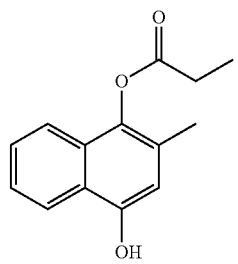

(4a)

2-Methyl-1,4-naphthohydroquinone Dipropionate (3a) (10 g) were in methanol (50 g) and water (5 g). Di-isopropylamine (2.5 g) was added and stirred at 40° C. When the reaction was complete, the mixture was quenched with $HCl_{(aq)}$ and then extracted with ethyl acetate. The organic layer was washed with brine for twice. It was concentrated under reduce pressure and the crude was re-crystallized with ethyl acetate (10 g) and Heptane (50 g), thereby obtaining 4.7 g the title compound (Yield: 58.8%, HPLC purity: 99.9%). The compound was characterized by $^1$H-NMR: δ 1.22-1.25, t, 3H; 2.16, s, 3H; 2.71-2.81, m, 2H; 6.75, s, 1H; 7.40-7.51, t, 2H; 7.63-8.11, d, 2H; 10.13, s, 1H.

EXAMPLE 5

Synthesis of 2-Methyl-3-phytyl-1,4-naphthohydroquinone Monoacetate (5)

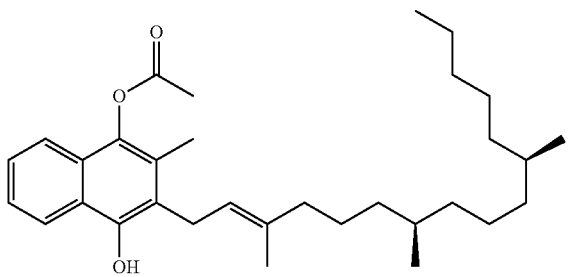

(5)

2-Methyl-1,4-naphthohydroquinone Monoacetate (4) (6 g), phytol (12.4 g) and $BF_3.OEt_2$ (0.78 g) were dissolved in ether (18 g) and heated to 80° C. for 2 hrs. Ether was removed by concentrated. MeOH (9 g) was added and extracted with Heptane (30 g). The organic layer was concentrated and purified by column chromatography (Heptan:ethyl acetate system), thereby obtaining 5.0 g the title compound (Yield: 37.9%, HPLC purity: 99.9%).

EXAMPLE 6

Synthesis of 2-Methyl-3-phytyl-1,4-naphthohydroquinone Monopropionate (5a)

(5a)

2-Methyl-1,4-naphthohydroquinone Monopropionate (4a) (4.1 g) phytol (7.85 g) and $BF_3.OEt_2$ (0.78 g) were dissolved in ether (12 g) and heated to 50° C. for 3 hrs. Ether was removed by concentrated. MeOH (4 g) was added and extracted with Heptane (20 g). The organic layer was concentrated and purified by column chromatography (Heptan:ethyl acetate system), thereby obtaining 1.7 g the title compound (Yield: 37.8%, HPLC purity: 99.9%).

EXAMPLE 7

Synthesis of Vitamin K1 (7)

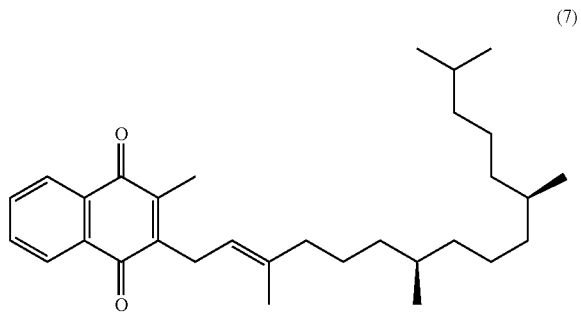 [SMILES: CC1=C(C/C=C(\C)CCC[C@H](C)CCC[C@H](C)CCCC(C)C)C(=O)c2ccccc2C1=O]

(7)

2-Methyl-3-phytyl-1,4-naphthohydroquinone Monoacetate (5) (0.6 g) was dissolved in Heptane (1.8 g) and methanol (3.6 g). KOH (0.2 g) and $Na_2S_2O_4$ (0.02 g) were dissolved in water (1.2 g) and then added to the mixture. The mixture was stirred at 18-20° C. for 1 hr and then quenched with acetic acid. The organic layer was washed with brine twice and purified by column chromatography (Heptane:ethyl acetate system), thereby obtaining 0.35 g the title compound (Yield: 63.6%, HPLC purity: >99.9%). The compound was characterized by $^1$H-NMR: δ 0.83-0.90, m, 12H; 1.03-1.54, m, 19H; 1.70-1.80, s, 3H (E,Z); 1.96, m, 2H; 2.21, s, 3H; 3.38-3.40, d, 2H; 5.01-5.04, m, 1H; 7.69-7.71,m,2H; 8.07-8.10, m, 2H.

EXAMPLE 8

Synthesis of Vitamin K1 (7)

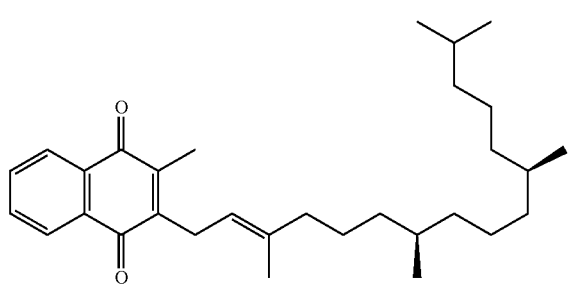

(7)

2-Methyl-3-phytyl-1,4-naphthohydroquinone Monopropionate (5a) (0.5 g) was dissolved in 95% EtOH (1.5 g) NaOH (0.04 g) and $Na_2S_2O_4$ (0.03 g) were dissolved in water (1.0 g) and then added to the mixture. The mixture was stirred at 25° C. for 4 hr and then quenched with acetic acid. The organic layer was washed with brine twice and purified by column chromatography (Heptane:ethyl acetate system), thereby obtaining 0.1 g the title compound (Yield: 22.7%, HPLC purity: 98.68%). The compound was characterized by $^1$H-NMR: δ 0.81-0.89, m, 12H; 1.01-1.60, m, 19H; 1.68-1.79, s, 3H (E,Z); 1.93-1.95, m, 2H; 2.20, s, 3H; 3.37-3.38, d, 2H; 5.00-5.02, m, 1H; 7.68-7.71,m,2H; 8.08-8.10, m, 2H.

According to this invention, the vitamin K1 is produced with 2-methyl-1,4-naphthoquinone as the starting material, instead of 2-methyl-1,4-naphthohydroquinone in the prior art. That is, the starting material of this invention is more stable than the starting material in the prior art. Preferably, the 2-methyl-1,4-naphthohydroquinone di-alkyl ester of this invention is produced through the first one-pot synthesis without isolating the 2-methyl-1,4-naphthohydroquinone, so that there is less by-product formed with the 2-methyl-1,4-naphthohydroquinone di-alkyl ester. More preferably, the final product, vitamin K1, can be produced through the second one-pot synthesis including hydrolysis and oxidation, and there is no metal oxidant used in the reaction. Therefore, the vitamin K1 of this invention is generated without metal residue and more safety on clinical application.

In summary, we have reported a method of making vitamin K1. The method of making vitamin K1 comprises performing hydrogenation in situ esterification through a first one-pot synthesis to produce 2-methyl-1,4-naphthohydroquinone di-alkyl ester from 2-methyl-1,4-naphthoquinone with a base catalyst, performing a first hydrolysis procedure to produce 2-methyl-1,4-naphthohydroquinone mono-alkyl ester from 2-methyl-1,4-naphthohydroquinone di-alkyl ester, performing a substitution procedure to have 2-methyl-1,4-naphthohydroquinone mono-alkyl ester react with phytol/phytol derivatives to generate 2-methyl-3-phytyl-1,4-naphthohydroquinone mono-alkyl ester, and performing a second one-pot synthesis to form vitamin K1 from 2-methyl-3-phytyl-1,4-naphthohydroquinone mono-alkyl ester. Preferably, according to this invention, before reacting with phytol or phytol derivatives, instead of 2-methyl-1,4-naphthohydroquinone, a more stable compound, 2-methyl-1,4-naphthoquinone, is employed as the starting material. Besides, through the first one-pot synthesis, both carbonyl group of the 2-methyl-1,4-naphthoquinone are performed hydrogenation and protected without isolating the 2-methyl-1,4-naphthohydroquinone. Therefore, we can efficiently decrease by-product with a clean reaction for producing 2-methyl-1,4-naphthohydroquinone di-alkyl ester. More preferably, after reacting with phytol or phytol derivatives, the vitamin K1 of this invention is produced from a second one-pot synthesis, wherein a second hydrolysis in situ oxidation procedure are accomplished in the second one-pot synthesis. Excluding simplifying the operation of the manufacturing, it is important that there is no metal oxidant used in the second one-pot synthesis, so that the vitamin K1 of this invention can be more safety for clinical patients. Therefore, comparing with those methods of making vitamin K1 in the prior art, this invention provides a more easily operating and more safety method for preparing vitamin K1.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method of making vitamin K1, comprising:
performing a first one-pot synthesis to produce 2-methyl-1,4-naphthohydroquinone di-alkyl ester of formula 2

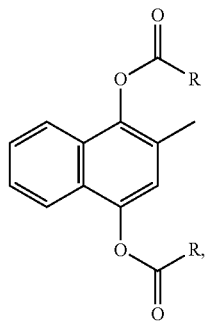

wherein R is C1-C20 alkyl group from 2-methyl-1,4-naphthoquinone with a base catalyst which is 4-dimethylaminopyridine (DMAP), and Pd/C and hydrogen, wherein said first one-pot synthesis includes a hydrogenation in situ esterification procedure;
performing a first hydrolysis procedure with an organic base to produce 2-methyl-1,4-naphthohydroquinone mono-alkyl ester of formula 3

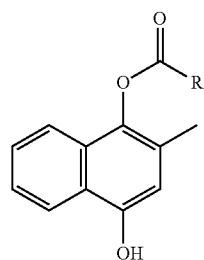

from the 2-methyl-1,4-naphthohydroquinone di-alkyl ester;
performing a substitution procedure with phytol derivative to generate 2-methyl-3-phytyl-1,4-naphthohydroquinone mono-alkyl ester of formula 4

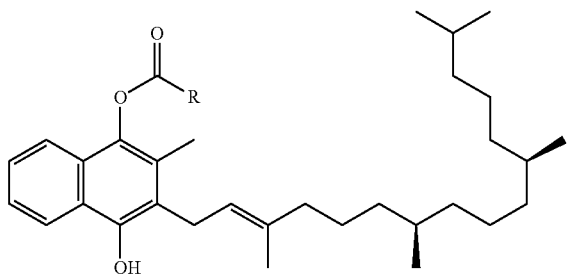

from the 2-methyl-1,4-naphthohydroquinone mono-alkyl ester; and
performing a second one-pot synthesis to form vitamin K1 from 2-methyl-3-phytyl-1,4-naphthohydroquinone mono-alkyl ester, wherein said second one-pot synthesis includes a second hydrolysis procedure and an oxidation procedure with KOH and $Na_2S_2O_4$ and without using metal oxidant.

2. The method of making vitamin K1 according to claim 1, wherein said organic base is an amine with stereo effect.

3. The method of making vitamin K1 according to claim 1, wherein said organic base is selected from the group consisting of diisopropylamine, and dicyclohexylamine.

4. The method of making vitamin K1 according to claim 1, wherein said substitution procedure is performed to have the 2-methyl-1,4-naphthohydroquinone mono-alkyl ester react with the phytol derivative selected from the group consisting of phytol, phytol ester, phytol halide, and isophytol.

5. A method of making vitamin K1, comprising:
reacting 2-methyl-1,4-naphthoquinone with carboxylic acid derivatives in the presence of a base catalyst which is 4-dimethylaminopyridine (DMAP) under hydrogen to form 2-methyl-1,4-naphthohydroquinone di-alkyl ester of formula 2;

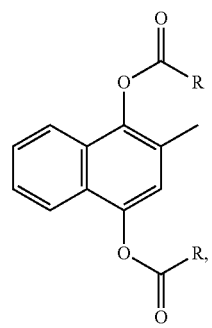

wherein R is C1-C20 alkyl group;
reacting said 2-methyl-1,4-naphthohydroquinone di-alkyl ester with an organic base to produce 2-methyl-1,4-naphthohydroquinone mono-alkyl ester of formula 3,

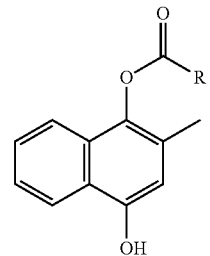

wherein said organic base is with stereo effect;
reacting said 2-methyl-1,4-naphthohydroquinone mono-alkyl ester with phytol derivatives to form 2-methyl-3-phytyl-1,4-naphthohydroquinone mono-alkyl ester of formula 4;

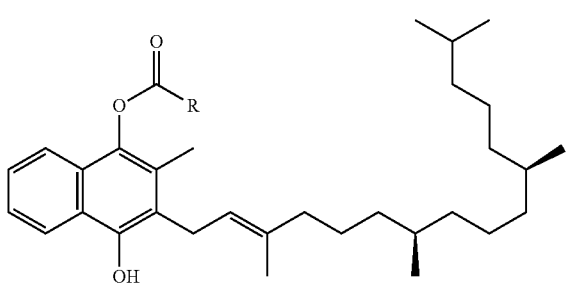

and
performing a hydrolysis-oxidation procedure to said 2-methyl-3-phytyl-1,4-naphthohydroquinone monoalkyl ester to form vitamin K1, wherein said hydrolysis-oxidation with KOH and $Na_2S_2O_4$ and is without metal oxidant.

6. The method of making vitamin K1 according to claim 5, wherein said carboxylic acid derivatives is selected from the group consisting of acyl anhydride, acyl halide active ester of HOSu (N-Hydroxysuccinimide), and active ester of HOBt (1-Hydroxybenzotriazole).

7. The method of making vitamin K1 according to claim 5, wherein said organic base is amine.

8. The method of making vitamin K1 according to claim 5, wherein said organic base is selected from the group consisting of diisopropylamine, and dicyclohexylamine.

9. The method of making vitamin K1 according to claim 5, wherein said phytol derivatives is selected from the group consisting of the phytol, phytol ester, phytol halide, and isophytol.

* * * * *